US00PP18274P2

(12) United States Plant Patent
Dekker

(10) Patent No.: US PP18,274 P2
(45) Date of Patent: Dec. 4, 2007

(54) ***CHRYSANTHEMUM* PLANT NAMED 'DEKCHIRONNE'**

(50) Latin Name: *Chrysanthemum×morifolium*
Varietal Denomination: Dekchironne

(75) Inventor: Cornelis W. Dekker, Hensbroek (NL)

(73) Assignee: Deeker Breeding B.V., Hensbroek (NL)

( * ) Notice: Subject to any disclaimer, the term of this patent is extended or adjusted under 35 U.S.C. 154(b) by 0 days.

(21) Appl. No.: 11/489,220

(22) Filed: Jul. 19, 2006

(51) Int. Cl.
*A01H 5/00* (2006.01)

(52) U.S. Cl. ..... Plt./287

(58) Field of Classification Search ..... Plt./287
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Dekchironne', characterized by its decorative pompon-type inflorescences with elongated oblong-shaped, yellow green-colored ray florets; strong and upright flowering stems; early and uniform flowering response; and good postproduction longevity.

1 Drawing Sheet

Botanical designation: *Chrysanthemum×morifolium.*
Cultivar denomination: 'Dekchironne'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Dekchironne'.

The new *Chrysanthemum* is a product of a planned breeding program conducted by the Inventor in Hensbroek, The Netherlands. The objective of the breeding program is to create new decorative-type *Chrysanthemum* cultivars with unique ray floret coloration and excellent postproduction longevity.

The new *Chrysanthemum* originated from a cross-pollination made by the Inventor in Hensbroek, The Netherlands on Feb. 6, 2004 of a proprietary selection of *Chrysanthemum×morifolium* identified as code number 42218, not patented, as the female, or seed, parent with a proprietary selection of *Chrysanthemum×morifolium* identified as code number 99.4137.01, not patented. The cultivar Dekchironne was discovered and selected by the Inventor as a flowering plant from within the progeny of the stated cross-pollination in a controlled environment in Hensbroek, The Netherlands on Oct. 15, 2004.

Asexual reproduction of the new *Chrysanthemum* by terminal cuttings in a controlled environment in Hensbroek, The Netherlands since November, 2004, has shown that the unique features of this new *Chrysanthemum* are stable and reproduced true to type in successive generations.

SUMMARY OF THE INVENTION

Plants of the cultivar Dekchironne have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekchironne'. These characteristics in combination distinguish 'Dekchironne' as a new and distinct cultivar of *Chrysanthemum:*

1. Decorative pompon-type inflorescences with elongated oblong-shaped, yellow green-colored ray florets.
2. Strong and upright flowering stems.
3. Early and uniform flowering response; plants flower about seven weeks after the start of photoinductive treatments.
4. Good postproduction longevity; plants maintain good substance for about three weeks in an interior environment.

Plants of the new *Chrysanthemum* differ from plants of the female parent selection in the following characteristics:

1. Plants of the new *Chrysanthemum* are less vigorous than plants of the female parent selection.
2. Plants of the new *Chrysanthemum* have smaller leaves than plants of the female parent selection.
3. Plants of the new *Chrysanthemum* have larger inflorescences than plants of the female parent selection.

Plants of the new *Chrysanthemum* differ from plants of the male parent selection in the following characteristics:

1. Plants of the new *Chrysanthemum* are less vigorous than plants of the male parent selection.
2. Plants of the new *Chrysanthemum* have larger leaves than plants of the male parent selection.
3. Plants of the new *Chrysanthemum* have larger inflorescences than plants of the male parent selection.
4. Plants of the new *Chrysanthemum* and the male parent selection differ in ray floret color as plants of the male parent selection have yellow-colored ray florets.

Plants of the new *Chrysanthemum* can be compared to plants of the *Chrysanthemum* cultivar Balloon, not patented. In side-by-side comparisons conducted in Hensbroek, The Netherlands, plants of the new *Chrysanthemum* differed from plants of the cultivar Balloon in the following characteristics:

1. Plants of the new *Chrysanthemum* had larger inflorescences than plants of the cultivar Balloon.
2. Inflorescences of plants of the new *Chrysanthemum* had 20% more ray florets than inflorescences of plants of the cultivar Balloon.
3. Plants of the new *Chrysanthemum* and the cultivar Balloon differed in ray floret color.

BRIEF DESCRIPTION OF THE PHOTOGRAPHS

The accompanying colored photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Dekchironne' grown as a disbud type.

The photograph at the bottom of the sheet are close-up views of the upper (left) and lower (right) surfaces of typical inflorescences and leaves of 'Dekchironne'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown during the spring in Hensbroek, The Netherlands, under commercial practice in a glass-covered greenhouse. Plants were initially given long day/short night treatments followed by short day/long night treatments to induce flower initiation and development. During the production of the plants, day temperatures ranged from 17.5° C. to 30° C., night temperatures ranged from 18.5° C. to 24° C. and light levels were about five kilolux. Plants were pinched once and were about nine weeks from planting when the photographs and the description were taken.

Botanical classification: *Chrysanthemum×morifolium* cultivar Dekchironne.

Parentage:

*Female, or seed, parent.*—Proprietary selection of *Chrysanthemum×morifolium* identified as code number 42218, not patented.

*Male, or pollen, parent.*—Proprietary selection of *Chrysanthemum×morifolium* identified as code number 99.4137.01, not patented.

Propagation:

*Type.*—Terminal vegetative cuttings.

*Time to initiate roots.*—About six to seven days at 20° C.

*Time to produce a rooted young plant.*—About 14 to 16 days at 20° C.

*Root description/habit.*—Fine; light brown in color; freely branching.

Plant description:

*Appearance/growth habit.*—Herbaceous decorative-type cut flower that is typically grown as a disbud type. Moderately vigorous growth habit.

*Flowering stem description.*—Aspect: Erect. Length: About 75 cm to 85 cm. Diameter: About 5 mm to 6 mm. Texture: Pubescent; longitudinally ridged. Color: Close to 144A to 144B.

*Foliage description.*—Arrangement: Alternate; simple. Length: About 6 cm to 12 cm. Width: About 5 cm to 8 cm. Apex: Rounded. Base: Attenuate. Margin: Palmately lobed; crenate.

*Texture, upper and lower surfaces.*—Pubescent, rough, leathery; veins prominent on lower surface.

*Color.*—Developing foliage, upper surface: Close to 144A. Developing foliage, lower surface: Close to 143C. Fully expanded foliage, upper surface: Darker than 137A; venation, close to 146B. Fully expanded foliage, lower surface: Darker than 146A; venation, 146C.

*Petiole.*—Length: About 1 cm to 1.5 cm. Diameter: About 3 mm. Texture, upper and lower surfaces: Pubescent. Color, upper and lower surfaces: Close to 146B.

Inflorescence description:

*Appearance.*—Decorative pompon-type inflorescence form with elongated oblong-shaped ray florets. Inflorescences borne on terminals, arising from leaf axils. Ray and disc florets develop acropetally on a capitulum. Inflorescences not fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to two weeks of long day/short night conditions after planting followed by photoinductive short day/long night conditions flower about seven weeks later when grown as a disbud.

*Postproduction longevity.*—In an interior environment, inflorescences and foliage with maintain good color and substance for about three weeks.

*Quantity of inflorescences.*—When grown as a spray type, freely flowering habit, about 12 to 15 inflorescences per flowering stem develop.

*Inflorescence size.*—Diameter: About 6 cm to 7 cm. Depth (height): About 3.5 cm to 4 cm. Disc diameter: About 2 mm.

*Inflorescence buds.*—Shape: Oblate. Height: About 6 mm. Diameter: About 9 mm. Color: Close to 144A.

*Ray florets.*—Length: About 1.5 cm to 2 cm. Width: About 8 mm to 12 mm. Shape: Elongated oblong. Aspect: Incurving. Apex: Emarginate. Base: Fused; tubular. Texture: Smooth, glabrous; satiny. Number of ray florets per inflorescence: About 500 arranged in numerous rows. Color: When opening, upper surface: Close to 151C. When opening, lower surface: Close to 154A. Fully opened, upper surface: Close to 154B; color becoming closer to 154C with development. Fully opened, lower surface: Close to 154A.

*Disc florets.*—Shape: Tubular, elongated. Length: About 7 mm. Diameter: About 1.5 mm. Number of disc florets per inflorescence: About 10; inconspicuous. Color: Immature: Close to 145D. Mature: Apex: 145A. Mid-section: 15D. Base: 145D.

*Reproductive organs.*—Androecium: Not observed. Gynoecium: Present on both ray and disc florets. Stigma length: About 5 mm. Stigma width: About 0.5 mm. Stigma shape: Bi-parted. Stigma color: Close to 154D; towards the apex, 154C to 154D.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekchironne' as illustrated and described.

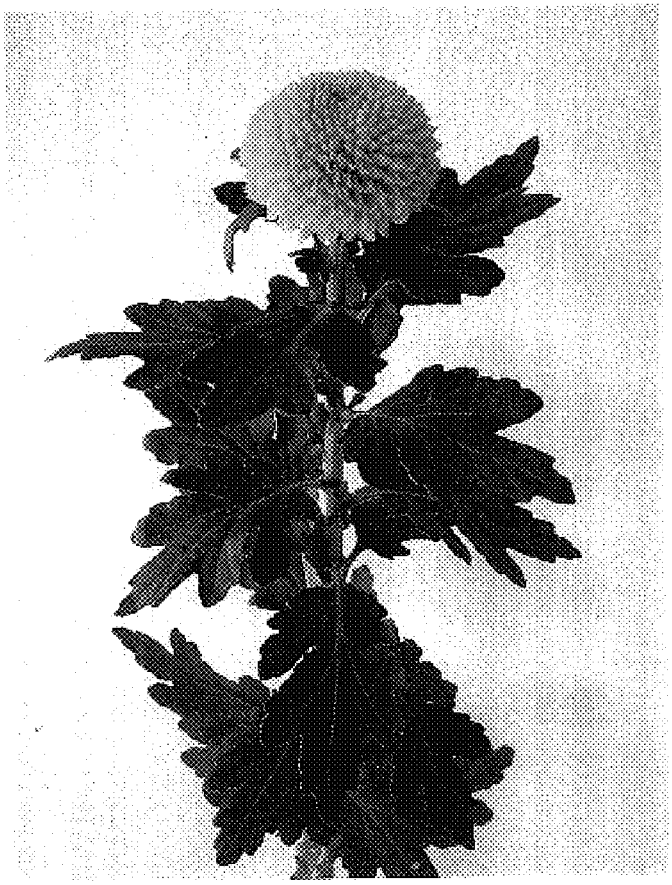
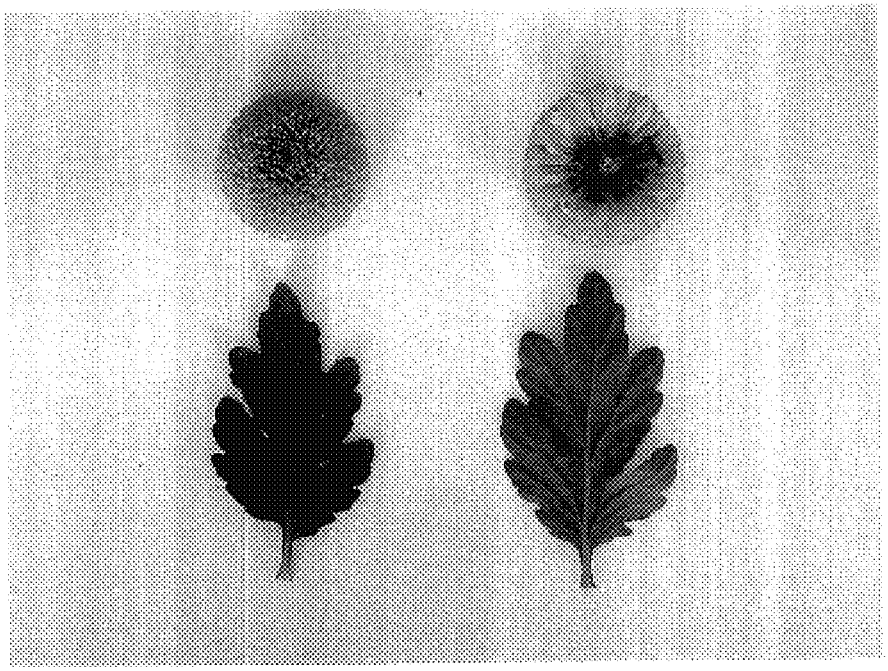

* * * * *